United States Patent [19]

Phillipps et al.

[11] Patent Number: 4,959,371
[45] Date of Patent: Sep. 25, 1990

[54] ISOQUINOLINE DERIVATIVES WITH ANTI-TUMOR ACTIVITY

[75] Inventors: Gordon H. Phillipps, Wembley; Michael G. Lester, Rickmansworth, both of United Kingdom

[73] Assignee: Glaxo Group Limited, London, England

[21] Appl. No.: 125,173

[22] Filed: Nov. 25, 1987

[30] Foreign Application Priority Data

Nov. 27, 1986 [GB] United Kingdom ............... 8628349
Nov. 27, 1986 [GB] United Kingdom ............... 8628351
Nov. 27, 1986 [GB] United Kingdom ............... 8628352

[51] Int. Cl.⁵ ............... C07D 221/18; A61K 31/445
[52] U.S. Cl. ............................... 514/283; 546/42
[58] Field of Search ........................ 546/42; 514/283

[56] References Cited

U.S. PATENT DOCUMENTS

| 3,336,317 | 8/1967 | Inman | 546/42 |
| 3,894,029 | 7/1975 | Winterfeldt | 546/42 |
| 4,029,659 | 6/1977 | Hannart | 546/42 |
| 4,033,966 | 7/1977 | Sawa | 546/42 |
| 4,042,591 | 8/1977 | Kaul | 546/42 |
| 4,087,426 | 5/1978 | Shamma | 546/42 |
| 4,399,282 | 8/1983 | Miyasaka | 546/42 |
| 4,434,290 | 2/1984 | Bisagni | 546/42 |
| 4,444,776 | 4/1984 | Bisagni | 546/42 |

FOREIGN PATENT DOCUMENTS

| A108620 | 5/1984 | European Pat. Off. | 546/42 |
| A161102 | 11/1985 | European Pat. Off. | 546/42 |
| A2129799 | 5/1984 | United Kingdom | 546/42 |
| A2175587 | 5/1985 | United Kingdom | 546/42 |

OTHER PUBLICATIONS

CA, vol, 75, 143961y(1971).
CA, vol. 77, 88260h (1972).
CA, vol. 83, 152267u (1975).
CA, vol. 83, 168484y (1975).
CA, vol. 92, 75895d (1980).
J. Heterocyclic Chem., vol. 15, pp. 1303-1307, (1978).
J. Organic Chemistry, vol. 37, No. 20, pp. 3111-3113 (1972).
"Reagents for Organic Synthesis", by Fieser et al., John Wiley & Sons, New York, (1967), pp. 682-684.
Patent Abstracts of Japan, vol. 8, No. 130(c-2290)[1567], 6-16-84.
"Synthesis and Reactions in the 1,2,3,4-Tetrahydroisoquinoline Series", C. R. Spray, (1980), pp. 161-162, 193-194, 208-221 and 243 (PhD thesis).

Primary Examiner—Mary C. Lee
Assistant Examiner—Robert C. Whittenbaugh
Attorney, Agent, or Firm—Bacon & Thomas

[57] ABSTRACT

There are provided compounds of general formula

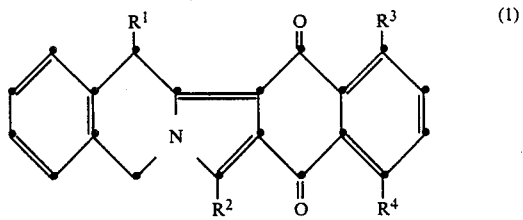

(wherein
$R^1$ is a hydrogen atom or a methyl group;
$R^2$ is a hydrogen or halogen atom or a methyl group;
and one of $R^3$ and $R^4$ is a hydrogen atom and the other is a group —$NR^5R^6$ [where $R^5$ is a hydrogen atom and $R^6$ is a group —$COCH_2NR^7R^8$ (wherein $R^7$ and $R^8$, which may be the same or different, each represents a hydrogen atom or a $C_{3-7}$ cycloalkyl group of a $C_{1-4}$ alkyl group optionally substituted by a hydroxyl or benzoyloxy group, or —$NR^7R^8$ forms a saturated heterocyclic amino group which has 5-7 ring members and optionally contains in the ring an oxygen or sulphur atom or a group —NH— or —N(R)— where R is a $C_{1-4}$ alkyl group optionally substituted by a hydroxyl group) or $R^6$ is a group —$COCH_2NH(CH_2)_nNR^7R^8$ (where n is an integer from 2 to 5 inclusive and $R^7$, $R^8$ and —$NR^7R^8$ are as defined above) or $R^6$ is a group —$N=CR^9R^{10}$ (where $R^9$ is a hydrogen atom or a $C_{1-4}$ alkyl group and $R^{10}$ is a $C_{1-4}$ alkyl group optionally substituted by a group —$NR^7R^8$ and $R^7$, $R^8$ and —$NR^7R^8$ are as defined above) or $R^5$ is a hydrogen atom or an acyl group and $R^6$ is a group —$(CH_2)_nNR^7R^8$ (where n, $R^7$, $R^8$ and —$NR^7R^8$ are defined above)]) and salts thereof. The compounds exhibit anti-cancer activity.

17 Claims, No Drawings

ISOQUINOLINE DERIVATIVES WITH ANTI-TUMOR ACTIVITY

This invention relates to new isoquinoline derivatives having anti-cancer activity, to processes for their preparation, to pharmaceutical compositions containing them, and to their use in medicine.

The invention thus provides compounds of the general formula (1)

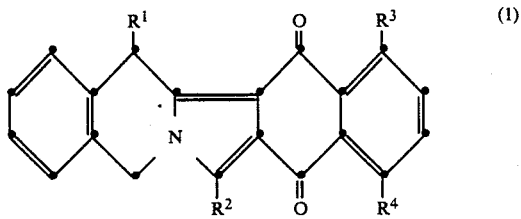

wherein
$R^1$ is a hydrogen atom or a methyl group;
$R^2$ is a hydrogen or halogen atom or a methyl group; and one of $R^3$ and $R^4$ is a hydrogen atom and the other is a group $-NR^5R^6$ [where $R^5$ is a hydrogen atom and $R^6$ is a group $-COCH_2NR^7R^8$ (wherein $R^7$ and $R^8$ which may be the same or different, each represents a hydrogen atom or a $C_{3-7}$ cycloalkyl group or a $C_{1-4}$ alkyl group optionally substituted by a hydroxyl or benzoyloxy group, or $-NR^7R^8$ forms a saturated heterocyclic amino group which has 5-7 ring members and optionally contains in the ring an oxygen or sulphur atom or a group $-NH-$ or $-N(R)-$ where R is a $C_{1-4}$ alkyl group optionally substituted by a hydroxyl group) or $R^6$ is a group $-COCH_2NH(CH_2)_nNR^7R^8$ (where n is an integer from 2 to 5 inclusive and $R^7$, $R^8$ and $-NR^7R^8$ are as defined above or $R^6$ is a group $-N=CR^9R^{10}$ (where $R^9$ is a hydrogen atom or a $C_{1-4}$ alkyl group and $R^{10}$ is a $C_{1-4}$ alkyl group optionally substituted by a group $-NR^7R^8$ and $R^7$, $R^8$ and $-NR^7R^8$ are as defined above or $R^5$ is a hydrogen atom or an acyl group and $R^6$ is a group $-(CH_2)_nNR^7R^8$ (where n, $R^7$, $R^8$ and $-NR^7R^8$ are as defined above)]; and salts, especially physiologically acceptable salts, thereof.

Compounds of formula (1) may exist as stereoisomers and/or tautomers and the invention is to be understood to include all such isomers of compounds of formula (1), including mixtures thereof.

Compounds of formula (1) may form salts with acids. It will he appreciated that, for pharmaceutical use, these salts should he physiologically acceptable, but other salts may find use, for example in the preparation of compounds of formula (1) as well as physiologically acceptable salts thereof.

Suitable physiologically acceptable salts of the compounds of general formula (1) are acid addition salts derived from inorganic and organic acids. Such salts include for example the hydrochlorides, hydrobromides, sulphates, phosphates, maleates, tartrates, citrates, benzoates, acetates, fumarates and succinates of the compounds of formula (1). References hereinafter to compounds of formula (1) are, unless the context demands otherwise, to the compounds themselves and to their physiologically acceptable salts.

When $R^3$ or $R^4$ contains a $C_{1-4}$ alkyl group this group may be straight or branched and may be, for example, methyl, ethyl, n-propyl, i-propyl, n-butyl, s-butyl or t-butyl.

Examples of alkyl groups represented by $R^7$ or $R^8$ in compounds of formula (1) include methyl, ethyl, propyl and butyl, optionally substituted by a hydroxy group, for example 2-hydroxyethyl. When $R^7$ or $R^8$ is a $C_{3-7}$ cycloalkyl group it may he for example cyclopropyl. Particular examples of $R^7$ and $R^8$ include methyl, ethyl, 2-hydroxyethyl and 2-benzoyloxyethyl.

When $-NR^7R^8$ in compounds of formula (1) represents a saturated heterocyclic amino group, this may have 5, 6 or 7 ring members and optionally contains in the ring an oxygen or sulphur atom or a group $-NH-$ or $-N(R)-$ where R may be for example a methyl or ethyl group optionally substituted by a hydroxyl group e.g. 2-hydroxyethyl. Examples of such groups represented by $-NR^7R^8$ are pyrrolidino, piperidino, hexamethyleneimino, piperazino, N-methylpiperazino, morpholino and thiomorpholino. Particular examples include morpholino and N-methylpiperazino.

When $R^5$ in compounds of formula (1) represents an acyl group it may be a benzoyl, phenyl $C_{1-6}$ alkanoyl (e.g. phenacetyl) or $C_{1-6}$ alkanoyl (e.g. acetyl group or a halogenated $C_{1-6}$ alkanoyl group (e.g. a trihaloacetyl group such as trifluoroacetyl However, $R^5$ is preferably a hydrogen atom.

Compounds of formula (1) in which $R^1$ represents a methyl group are generally preferred.

When the group $R^2$ in general formula (1) is a halogen atom it may be a fluorine, chlorine, bromine or iodine atom, in particular a bromine atom. However, in general, $R^2$ is preferably a methyl group, or more preferably a hydrogen atom.

When $R^6$ is a group $-COCH_2NR^7R^8$ particular examples of the group $-NR^5R^6$ include $-NHCOCH_2N(CH_3)_2$, $-NHCOCH_2N(CH_2CH_3)_2$, $-NHCOCH_2NHCH_2CH_2OH$,

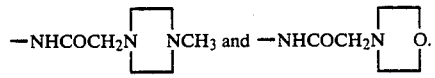

When $R^6$ is a group $-COCH_2NH(CH_2)_nNR^7R^8$ particular examples of the group $-NR^5R^6$ include $-NHCOCH_2NHCH_2CH_2N(CH_3)_2$ and $-NHCOCH_2NHCH_2CH_2N(CH_2CH_3)_2$.

When $R^6$ is a group $-N=CR^9R^{10}$ particular examples of the group $-NR^5R^6$ include
$-NHN=C(CH_3)CH_2CH_2N(CH_3)_2$,
$-NHN=C(CH_3)CH_2CH_2N(CH_2CH_3)_2$,
$-NHN=C(CH_3)CH_2N(CH_3)_2$,
$-NHN=C(CH_3)CH_2N(CH_2CH_3)_2$ and
$-NHN=C(CH_3)_2$.

When $R^6$ is a group $-(CH_2)_nNR^7R^8$ particular examples of the group $-NR^5R^6$ include $-NHCH_2CH_2N(CH_3)_2$, $-NHCH_2CH_2N(CH_2CH_3)_2$ and $-NHCH_2CH_2N(CH_2CH_3)CH_2CH_2OH$.

Compounds of formula (1) in which $R^3$ is a hydrogen atom are generally preferred.

A particularly preferred group of compounds according to the invention comprises those of formula (1) in which:
$R^1$ is a methyl group;
$R^2$ is a hydrogen atom;
$R^3$ is a hydrogen atom; and $R^4$ is a group $-NH(CH_2)_nNR^7R^8$ (where n is an integer from 2-5, preferably 2, and $R^7$ and $R^8$ are as defined above, especially methyl, ethyl or 2-hydroxyethyl); and the salts thereof.

Another particularly preferred group of compounds according to the invention comprises those of formula (1) in which:

$R^1$ is a methyl group;
$R^2$ is a hydrogen atom;
$R^3$ is a hydrogen atom; and
$R^4$ is a group $-NHN=CR^9R^{10}$ (where $R^9$ and $R^{10}$ are as defined above); and the salts thereof. Such compounds in which $R^9$ is methyl and $R^{10}$ is methyl, diethylaminomethyl or diethylaminoethyl are especially preferred.

Important active compounds of formula (1) include 5,8,13,14-tetrahydro-9-(2-((N-ethyl,N-2-hydroxyethyl)amino)ethylamino)-14-methylbenz[5,6]isoindolo[2,1-b]isoquinoline-8,13-dione and its physiologically acceptable salts, e.g. the hydrochloride salt, and 4-diethylaminobutan-2-one, 5,8,13,14-tetrahydro-8,13-dioxo-14-methylbenz[5,6]isoindolo[2,1-b]isoquinolin-9-yl]hydrazone and its physiologically acceptable salts, e.g. the hydrochloride salt.

The compounds of formula (1) possess good anticancer-antitumor activity, against tumours such as carcinomas, sarcomas and hepatomas.

Thus, when a compound of formula (1) is administered intraperitoneally, intravenously or orally to mice with a subcutaneous tumour arising from an implant of S180 cells, subsequent examination has shown that tumour growth has been significantly reduced and in some cases total regression of the tumour has occurred. Activity against L1210 (mouse lymphocytic leukaemia, grown ascitally) has also been shown.

Compounds according to the invention also have improved water solubility and increased stability in aqueous solution over isoquinoline compounds reported in EP-A-No. 108620 and EP-A-No. 161102 as having anti-cancer activity. Solubility in water is, of course, an important feature when it desired to formulate a pharmaceutical for parenteral administration.

According to a further aspect of the present invention we provide a compound of formula (1) or a physiologically acceptable salt thereof for use in the treatment of the human or non-human animal body to combat cancerous tumors such as carcinomas, sarcomas and hepatomas therein.

According to a yet further aspect of the present invention we provide the use of a compound of formula (1) or a physiologically acceptable salt thereof for the manufacture of a therapeutic agent for the treatment of the human or non-human animal body to combat cancer, particularly tumours, therein.

According to a still further aspect of the present invention we provide a method of treatment of the human or non-human animal body to combat cancers, particularly tumours, therein, which method comprises administering to the said body an effective amount of a compound of formula (1) or a physiologically acceptable salt thereof.

It will be appreciated that the compounds according to the invention may advantageously be used in conjunction with one or more other therapeutic agents, such as for example anti-emetic agents, immunosuppressive agents or different anti-cancer agents. It is to be understood that the present invention covers the use of a compound of formula (1) or a physiologically acceptable salt thereof in combination with one or more other therapeutic agents.

In a further aspect of the present invention we provide a pharmaceutical composition comprising as an active ingredient a compound of formula (1) or a physiologically acceptable salt thereof together with one or more pharmaceutical carriers or excipients.

The compounds according to the invention may be formulated for administration in any convenient way, and the invention therefore also includes within its scope pharmaceutical compositions comprising a compound of formula (1) or a physiologically acceptable salt thereof adapted for use in human or veterinary medicine. Such compositions may be presented for use in conventional manner in admixture with one or more physiologically acceptable carriers or excipients. The compositions may optionally further contain one or more other therapeutic agents such as a different anti-cancer agent or an anti-emetic agent or an immunosuppressive agent.

Thus, the compounds according to the invention may be formulated for oral, buccal, topical, rectal or, preferably, parenteral administration (e.g. by bolus injection or intravenous infusion).

Injections are sterile products and may be presented in unit dose form, for instance as ampoules, vials, small volume infusions or pre-filled syringes, or in multi-dose containers, for example, with an added preservative. The compositions may take such forms as solutions, suspensions or emulsions in aqueous or non-aqueous vehicles, and may contain formulatory agents such as anti-oxidants, buffers, bulking agents, chelating agents, antimicrobial agents, solubilising agents, surfactants and/or tonicity adjusting agents. Alternatively, the active ingredient (with our without added substances) may be in a dry form for constitution with a suitable vehicle, e.g. sterile pyrogen free water or dextrose, before use. The dry solid presentation may be prepared by filling a sterile powder aseptically into individual sterile containers or by filling a sterile solution aseptically into each container and freeze-drying.

The compounds according to the invention may also be formulated as compositions for oral administration. As tablets or capsules, they may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents surfactants, non-aqueous vehicles, preservatives, sugars, sweetening agents, buffers, colours, antioxidants and/or flavours. The compounds may also be formulated as suppositories, e.g. containing conventional suppository bases such as cocoa butter or other glycerides.

For buccal administration the compositions may take the form of tablets or lozenges formulated in conventional manner.

For topical administration the compounds according to the invention may be formulated as ointments, creams, lotions, powders, pessaries sprays, aerosols or drops (e.g. eye or nose drops). Ointments and creams may, for example, be formulated with an aqueous or oily base with the addition of suitable thickening and/or gelling agents. Such bases may thus, for example, include water and/or an oil such as liquid paraffin or a vegetable oil such as arachis oil or castor oil. Lotions may be formulated with an aqueous or oily base and will in general also contain one or more emulsifying agents, stabilising agents, dispersing agents, suspencing agents, thickening agents and/or colouring agents. Powders may be formed with the aid of any suitable powder base, for example talc, lactose or starch. Drops may be formulated with an aqueous or non-aqueous base also comprising one or more dispersing agents, solubilising agents or suspending agents. Aerosol sprays are conveniently delivered from pressurised packs, with the use of a suitable propellant, e.g. dichlorodifluoromethane, trichlorofluoromethane, dichlorotetrafluoroethane, carbon dioxide or other suitable gas.

The compositions may contain 0.1–100% of the active material.

It may be possible to target a compound of the invention to a tumour by including in the composition specialised drug carrier systems such as liposomes, albumen microspheres or monoclonal antibodies.

For systemic administration the daily dosage as employed for adult human treatment will generally be within the range of from 5 mg to 5000 mg, preferably 50 mg to 2000 mg, which may be administered in 1 to 5 divided daily doses, for example, depending on the route of administration and the condition of the patient. When the compositions comprise dosage units, each unit will preferably contain 10 mg to 2000 mg of active ingredient. For example 50 mg to 1000 mg.

For topical administration the daily dosage as employed for adult human treatment will generally range from 0.1 mg to 1000 mg, depending on the condition of the patient.

The compounds useful according to the invention may conveniently be prepared by the processes described in the following, wherein the various groups and symbols are as defined for formula (1) unless otherwise specified.

Thus, according to one process (A), a compound of formula (1) may be prepared by reacting a compound of formula (2)

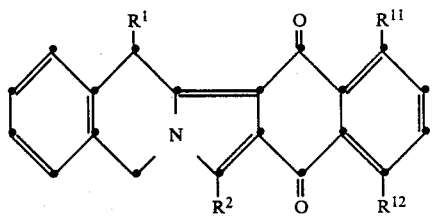

(where one of $R^{11}$ and $R^{12}$ is a hydrogen atom and the other is a group $-NHR^5$) to convert the group $-NHR^5$ into a group $-NR^5R^6$ to produce a compound of formula (1).

In one embodiment of the process, a compound of formula (2) in which $R^5$ is trifluoroacetyl is reacted with an amine $R^7R^8N(CH_2)_nL$ (where L is a leaving group such as a halogen atom, e.g. chlorine, bromine or iodine), followed, if desired, by deacylation to provide a compound of formula (1) in which $R^5$ is a hydrogen atom and $R^6$ is a group $-(CH_2)_nNR^7R^8$ and then, if desired, followed by acylation to provide the corresponding compound of formula (1) in which $R^5$ is an acyl group.

The reaction involving the amine $R^7R^8N(CH_2)_nL$ may be effected in the presence of a suitable solvent, for example acetonitrile or a ketone such as acetone, a substituted amide e.g. dimethylformamide or dimethylacetamide or a halogenated hydrocarbon e.g. dichloromethane at a temperature from ambient to the reflux. The reaction is preferably carried out in the presence of a base e.g. an alkali metal hydroxide such as sodium hydroxide or potassium hydroxide.

The acylation and deacylation reactions may be carried out using standard procedures. Thus, for example, acylation may be effected using an acylating agent such as an acid of formula $R^5OH$ or a reactive derivative thereof, such as an acid halide (e.g. acid chloride), anhydride or activated ester. The acylation reaction may be effected in an aqueous or non-aqueous reaction medium, conveniently at a temperature in the range of $-20°$ to $+100°$ C., e.g. room temperature. Suitable solvents which may be employed in the acylation reaction include ketones (e.g. acetone), amides (e.g. N,N-dimethylformamide), ethers (e.g. diethyl ether or tetrahydrofuran), nitriles (e.g. acetonitrile), hydrocarbons such as halogenated hydrocarbons (e.g. methylene chloride), and esters (e.g. ethyl acetate), as well as mixtures of such solvents. Deacylation may be effected by basic hydrolysis e.g. using an alkali metal hydroxide such as sodium hydroxide or potassium hydroxide in aqueous alcohol (e.g. aqueous methanol) or using aqueous $NH_3$, or by acid hydrolysis e.g. using a mineral acid such as hydrochloric acid.

In a further embodiment of the process, a compound of formula (2) in which $R^5$ is a hydrogen atom is treated with sodium nitrite in aqueous hydrochloric acid at reduced temperature (e.g. 0° C.) followed by treatment with a reducing agent such as a tin (II) compound (e.g. stannous chloride) in concentrated hydrochloric acid at reduced temperature (e.g. 0° to 5° C.) to provide a hydrazine of formula (3)

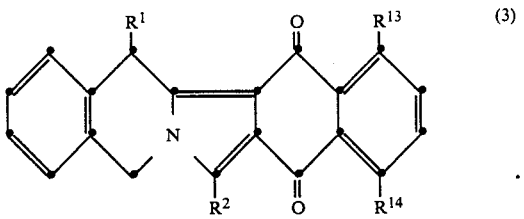

wherein one of $R^{13}$ and $R^{14}$ is a group $-NHNH_2$ and the other is a hydrogen atom.

The hydrazine of formula (3) may be converted to a compound of the invention in which $R^5$ is a hydrogen atom and $R^6$ is a group $-N=CR^9R^{10}$ under standard conditions. Thus, for example, the compound of formula (3) may be treated with an aldehyde or ketone $R^9R^{10}C=O$ in a suitable solvent, e.g. an ether such as dioxan at ambient temperature to provide the appropriate compound of formula (1). This reaction is preferably carried out under acidic conditions e.g. using p-toluene-sulphonic acid.

Conveniently, the compounds of the invention in which $R^5$ is a hydrogen atom and $R^6$ is $-N=CR^9R^{10}$ are prepared direct from suitable compounds of formula (2) without isolating the intermediate hydrazines of formula (3).

In another embodiment of the process, a compound of formula (2) in which $R^5$ is a hydrogen atom is treated with an acylating agent, such as an acid anhydride of the formula O(COCH$_2$L)$_2$ (where L is a leaving group as defined above or represents a hydrocarbylsulphonyloxy group such as methanesulphonyloxy or p-toluenesulphonyloxy) in the presence of a base such as triethylamine at ambient temperature followed by treatment with a base such as sodium hydroxide to provide a compound of formula (4)

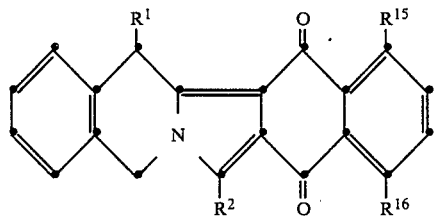

(4)

where one of R$^{15}$ and R$^{16}$ is a hydrogen atom and the other is a group —NHCOCH$_2$L (where L is as defined just above)].

The compound of formula (4) may be converted to a compound of the invention in which R$^5$ is a hydrogen atom and R$^6$ is a group —COCH$_2$NR$^7$R$^8$ or —COCH$_2$NH(CH$_2$)$_n$NR$^7$R$^8$ by reaction with an amine R$^7$R$^8$NH or a diamine R$^7$R$^8$N(CH$^2$)$_n$NH$_2$ respectively. The reaction may be effected in the presence of a suitable solvent, e.g. acetonitrile, a ketone such as acetone, a substituted amide such as dimethylformamide or dimethylacetamide or a halogenated hydrocarbon such as dichloromethane at a temperature from ambient to reflex.

Alternatively, the intermediates of formula (4) may be prepared by condensing a quinone of formula (5)

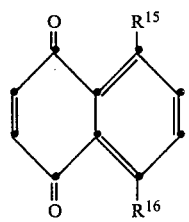

(5)

(where R$^{15}$ and R$^{16}$ are as defined above) with a compound of formula (6)

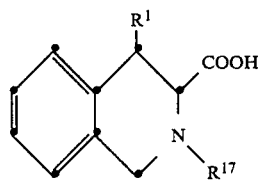

(6)

(where R$^{17}$ is a hydrogen atom or a group —CHO or COCH$_3$) in the presence of an alkanoic acid anhydride, such as acetic anhydride, at an elevated temperature, e.g. 75°-100° C.

Intermediates of formula (2) in which R$^5$ is a trifluoroacetyl group may be prepared from the corresponding intermediates of formula (2) in which R$^5$ is a hydrogen atom by acylation using trifluoroacetic acid or a reactive derivative thereof such as the corresponding halide, anhydride or activated ester under the acylation conditions described above.

The primary amines of formula (2) (i.e. where R$^5$ is a hydrogen atom) may be prepared by reducing the corresponding nitro compound of formula (7)

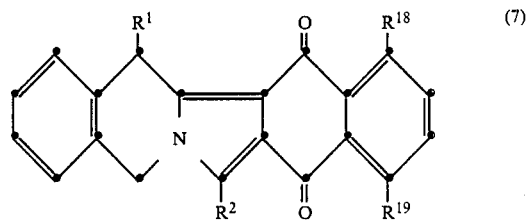

(7)

(where one of R$^{18}$ and R$^{19}$ is a group —NO$_2$ and the other is a hydrogen atom).

The reduction may be effected using a reducing agent which will reduce the nitro group to an amino group but leave the other reducable sites unaffected. A suitable reducing agent which may conveniently be employed is tin (II) chloride, and the reaction may be effected in a suitable solvent such as an alcohol e.g. methanol at an elevated temperature e.g. reflux, and in the presence of a strong acid e.g. concentrated hydrochloric acid.

The primary amines of formula (2) may also be prepared by hydrolysing an amide of formula (4) in which L is a halogen atom e.g. iodine.

The hydrolysis may be effected under acidic conditions using conventional means. Thus, for example, the hydrolysis may be carried out using aqueous mineral acid e.g. aqueous hydrochloric acid.

The nitro compounds of formula (7) may be prepared by condensing a quinone of formula (8)

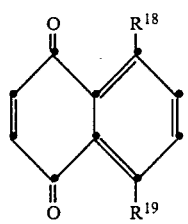

(8)

(where R$^{18}$ and R$^{19}$ are as defined above) with a compound of formula (6) under the conditions previously described for the preparation of compounds of formula (4) from compounds of formulae (5) and (6).

According to another process (8) compounds of formula (1) in which R$^2$ is a halogen atom may be prepared by halogenating a corresponding compound in which R$^2$ is a hydrogen atom. Standard halogenation procedures may be used, for example reaction with a N-chloro, N-bromo or N-iodoimide, e.g. N-chloro, N-bromo- or N-iodosuccinimide in an inert solvent such as dichloromethane at ambient temperature, or by reaction with perchloryl fluoride.

It will be appreciated that certain of the above reactions cannot be effected when the relevant intermediate contains a group R$^2$ where R$^2$ is a halogen atom. In these circumstances the reaction is effected using the corresponding intermediate in which R$^2$ is a hydrogen atom and the product of the reaction converted to the appropriate intermediate in which R$^2$ is a halogen atom using standard halogenation procedures such as those described just above.

The intermediates of formulae (2), (3), (4) and (7) are novel compounds and thus according to a still further aspect of the invention we provide a compound of general formula (9)

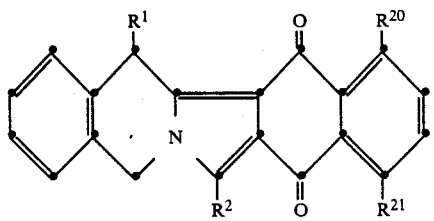

wherein one of $R^{20}$ and $R^{21}$ is a hydrogen atom and the other is a group —$NHR^5$, —$NHNH_2$, —$NHCOCH_2L$ or —$NO_2$ and where $R^1$, $R^2$, $R^5$ and L are as hereinbefore defined).

Compounds of formulae (6) and (8) are either known compounds or may be prepared using methods analogous to those used for the preparation of the known compounds described in EP-A-No. 161102.

Intermediates of formula (5) may be prepared from the known compounds of formula (5) in which $R^{15}$ or $R^{16}$ is a primary amino group by reaction with an anhydride of formula $O(COCH_2L)_2$ (where L is as previously defined) under the general conditions described above for the preparation of compounds of formula (4) from compounds of formula (2).

Physiologically acceptable salts of the compounds of general formula (1) may be prepared by reaction of a compound of general formula (1) with an appropriate acid in the presence of a suitable solvent. Thus for example, the hydrochloride salt of a compound of formula (1) may be prepared by reacting a compound of formula (1) with hydrochloric acid in an ether solvent such as diethyl ester tetrahydrofuran or dioxan or water.

When a specific enantiomer of formula (1) is required, this may be prepared by conventional methods of resolution known per se. Thus, for example, racemic compounds of the invention may be resolved as salts with optically active acids, e.g. (L)-(+)- or (D)-(—)-tartaric acid. Alternatively, optically active compounds of formula (1) may be prepared from optically active intermediates, e.g. optically active intermediates of formula (6). Racemic compounds of formula (6) in which $R^{17}$ is hydrogen may be resolved for example as salts with optically active acids as above or with optically active bases, e.g. (+)-dehydroabietylamine or (R)-(+)- or (S)-(—)-α-methylbenzylamine.

Compounds of formula (6) in which $R^{17}$ is CHO or $COCH_3$ may be similarly resolved as salts with optically active bases.

The following non-limiting Examples illustrate the invention. All temperatures are in °C. Unless otherwise stated all UV spectral data relate to solutions in ethanol of the compounds concerned.

Intermediate 1

5,8,13,14-Tetrahydro-14-methyl-9-nitrobenz[5,6]isoindolo[2,1-b]-isoquinoline-8,13-dione A mixture of 5-nitro-1,4-naphthoquinone (4.7 g) and N-formyl-4-methyl-3-tetrahydroisoquinolinecarboxylic acid (2.4 g) suspended in acetic anhydride (15 ml) was stirred and heated at 70°-75° for 2½ hours. The mixture was cooled and the solid formed was collected by filtration, washed with acetic anhydride, then with ether and finally dried to give the title compound (5.4 g) as a yellow crystalline solid. N.m.r. in DMSO$_{d6}$(ppm) δ 1.49(14-C$\underline{H}_3$);4.88(14-$\underline{H}$); 5.37, 5.47(5-C$\underline{H}_2$); 8.39(10-$\underline{H}$). U.v. $\lambda_{max}$ 246 nm, $E_1^1$481; 376 nm, $E_1^1$83.

Intermediate 2

5,8,13,14-Tetrahydro-9-amino-14-methylbenz[5,6]isoindolo[2,1-b]-isoquinoline-8,13-dione Intermediate 1 (11.4 g) and stannous chloride (71 g) suspended in a mixture of ethanol (670 ml) and 10N-hydrochloric acid (200 ml) were stirred and heated under reflux for 3½ hours. The mixture was then cooled in ice and the solid formed was collected by filtration and washed with 10N-hydrochloric acid (30 ml) whereupon further solid was deposited. This was collected and washed with hydrochloric acid as before. The combined solids were suspended in dichloromethane (1 liter) and treated with excess 2N-sodium hydroxide solution which resulted in the formation of a bright red suspension. This suspension was stirred vigorously at 20° until all of the red solid had decomposed and given rise to a two-phase solution. Separation of the organic phase, drying and evaporation followed by trituration of the residue with ether afforded the title compound (9.2 g) as an orange crystalline solid. N.m.r. in CDCl$_3$ (ppm) δ 1.58(14-C$\underline{H}_3$); 4.97(14-$\underline{H}$); 5.13, 5.25(5-C$\underline{H}_2$): 6.88(10-$\underline{H}$). U.v. $\lambda_{max}$ 234 nm, $E_1^1$211; 257 nm, $E_1^1$ 889; 368 nm, $E_1^1$282; 454 nm, $E_1^1$576.

Intermediate 3

N-[5,8,13,14-Tetrahydro-8,13-dioxo-14-methylbenz[5,6]isoindolo[2,1-b]-isoquinolin-9-yl]trifluoroacetamide Intermediate 2 (4 g suspended in diochloromethane (100 ml) was treated at 20° with trifluoroacetic anhydride (3.4 ml). After standing in the absence of moisture for 30 minutes the mixture was concentrated to dryness. The residue was triturated with ether and the resultant yellow solid was collected by filtration, washed with ether and dried to give the title compound (4.6 g). N.m.r. in CDCl$_3$(ppm) δ 1.58(14-C$\underline{H}_3$); 4.97(14-$\underline{H}$); 5.19,5.29 (5-C$\underline{H}_2$); 8.17(10-$\underline{H}$); 13.96(-N$\underline{H}$). U.v. $\lambda_{max}$ 251 nm, $E_1^1$523; 388 nm, $E_1^1$172.

Intermediate 4

N-[5,8,13,14-Tetrahydro-8,13-dioxo-14-methylbenz[5,6]isoindolo[2,1-b]isoquinolin-9-yl]-1-chloroacetamide Intermediate 2 (0.65 g) dissolved in dichloromethane (6 ml) containing triethylamine (16 ml) was treated with chloroacetic anhydride (1.03 g) at 20° for 2 hours. The mixture was washed with aqueous sodium bicarbonate, dried and evaporated. The residue was chromatographed on silica gel, eluting with a mixture of dichloromethane and acetone (100:1) to give the title compound (0.7 g). N.m.r. in DMSO-d$_6$ δ 1.59(14-C$\underline{H}_3$); 4.28 (C$\underline{H}_2$Cl); 4.97 (14-$\underline{H}$); 5.18, 5.27 (5-C$\underline{H}_2$); 8.10 (10-$\underline{H}$); 13.41 (N$\underline{H}$). U.v. $\lambda_{max}$ 253 nm, $E_1^1$ 957; 393 nm, $E_1^1$ 297.

Intermediate 5

N-[5,8,13,14-Tetrahydro-8,13-dioxo-14-methylbenz[5,6]isoindolo[2,1-b]isoquinolin-9-yl]-iodoacetamide Intermediate 4 (0.65 g) and sodium iodide (2.4 g) in acetone (200 ml) were heated under reflux for 4 hours. After removal of acetone the residue was washed thoroughly with water and dried to give the title compound (0.75 g) which was identical to the 9-isomer of Intermediate 11.

Intermediate 6

N-[5-(Chloroacetyloxy)-1-naphthalenyl]-1-chloroacetamide

5-Amino-1-naphthol (26 g) in dry tetrahydrofuran (260 ml) was treated with triethylamine (49 ml), cooled in ice then treated portionwise with stirring with chloroacetic anhydride (60 g). The mixture was allowed to warm to 20°, then after 3 hours was poured into water (1500 ml) to yield a mauve precipitate which was collected, washed with water and dried under suction to yield the title compound (51 g), m.p. 176°.

Intermediate 7

N-[5-Hydroxy-1-naphthalenyl]-1-chloroacetamide

Intermediate 6 (31.2 g) suspended in methanol (310 ml) was cooled in ice and stirred during the gradual addition of an aqueous solution of 0.1N sodium hydroxide (40 ml). After the addition (10 min) the mixture was kept at 4° for a further 5 mins then neutralized to pH 5 with 2N-hydrochloric acid. Water (50 ml) was added, the mixture was filtered and the filtrate was then diluted with water (2 liters) and sufficient ice to cool the mixture to 0°. The precipitated crystalline product was then collected by filtration washed with water and dried under suction to give the title compound (16 g), m.p. 191°.

Intermediate 8

N-5-Hydroxy-1-naphthalenyl]-1-iodoacetamide

Intermediate 7 (16.5 g) was added to a solution of sodium iodide (103 g) in acetone (520 ml) at 20°. The resulting solution was stoppered and left at 20° for 18 hours then evaporated and the residue shaken with water (750 ml) and filtered to yield a solid which was washed with water and dried under suction to give the title compound (21.5 g), m.p. 166°.

Intermediate 9

N-[5,8-Dioxo-5,8-dihydro-1-naphthalenyl]-1-iodoacetamide

Intermediate 8 (6 g) dissolved in methanol (300 ml) was surrounded by a cold water bath and stirred during the addition over 1 minute of a solution of potassium nitrosodisulphonate (10.8 g) and potassium dihydrogen phosphate (2.4 g) in water (600 ml). After the addition the mixture was stirred for a further 6 minutes then filtered (Hyflo). The filtrate was diluted with saturated brine (1500 ml) and extracted with dichloromethane (4×300 ml) then tetrahydrofuran (3×500 ml). The extracts were combined, the resulting aqueous layer was separated diluted with brine and re-extracted with 50% tetrahydrofuran/ethyl acetate. The combined organic solutions were dried (MgSO$_4$) and evaporated to yield the title compound (5 g). N.m.r. in CDCl$_3$ (ppm) δ 3.97 (C$\underline{H}_2$I); 6.98 (C$\underline{H}$=C$\underline{H}$)

Intermediate 10

N-[5,8,13,14-Tetrahydro-8,13-dioxobenz[5,6]isoindolo[2,1-b]isoquinolin-9- and 12-yl]-1-iodoacetamide Intermediate 9 (5 g) and 2-formyl-1,2,3,4-tetrahydro-3-isoquinolinecarboxylic acid (1.5 g) in acetic anhydride (30 ml) were heated at 100° for 10 minutes then kept overnight at 20°. The resulting precipitate was collected by filtration, washed with acetic anhydride, then ether, to yield the title compound (2.0 g) as a mixture of 9- and 12-isomers, m.p. >300°.

Intermediate 11 was prepared in a similar manner.

Intermediate 11

N-[5,8,13,14-Tetrahydro-8,13-dioxo-14-methylbenz[5,6]isoindolo[2,1-b]isoquinolio-9- and 12-yl]-1-iodoacetamide The title compounds were obtained as a mixture from Intermediate 9 (15 g) and 4-methyl-2-formyl-1,2,3,4-tetrahydro-3-isoquinoline-3-carboxylic acid (4.7 g). Separation of the 9- and 12-isomers was achieved by chromatography on silica gel eluting with 1% acetone in dichloromethane to give the 9-isomer of the title compound (0.9 g), N.m.r. in DMSO ppm δ 1.50 (C$\underline{H}_2$); 4.08 (C$\underline{H}_2$I); 4.83(14-H); 5.34 and 5.44 (5-CH$_2$) and the 12-isomer of the title compound (2.9 g), N.m.r. in DMSD (ppm) δ 1.52 (C$\underline{H}_3$); 4.11(C$\underline{H}_2$); 4.89(14-H); 5.37 and 5.44 (5-C$\underline{H}_2$).

EXAMPLE 1

4-Diethylaminobutan-2-one, [5,8,13,14-tetrahydro-8,13-dioxo-14-methylbenz[5,6]isoindolo[2,1-b]isoquinolin-9-yl]hydrazone Intermediate 2 (2.6 g) suspended in 10N hydrochloric acid (26 ml) was cooled to 5° then stirred during the gradual addition of a solution of sodium nitrite (0.66 g) in water (15 ml), maintaining the temperature below 5°. After the addition, the resulting orange suspension was added at 0° to a stirred solution of stannous chloride (9 g) in 10N hydrochloric acid (27 ml). The resulting yellow solid was collected by filtration then suspended in water (250 ml) and treated with sufficient 2N sodium hydroxide solution to bring the pH of the solution to ca. 10. The precipitated solid was then extracted with ethyl acetate, the extracts washed with brine, dried and evaporated. The residue was dissolved in dioxan (85 ml) and then treated with 4-diethylamino butan-2-one (5.1 g) and p-toluenesulphonio acid (1.4 g) and stirred at 20° for 4 hours. The mixture was then diluted with ether and brine and basified with excess aqueous sodium bicarbonate. Evaporation of the organic layer followed by drying and evaporation of the solvents afforded the crude product which was purified by chromatography on silica gel, eluting with a mixture of chloroform and in ethanol (10:1) to give the title compound as a orange solid (0.8 g). N.m.r. in CDCl$_3$(ppm) δ 1.06(N(CH$_2$C$\underline{H}_3$)$_2$); 1.53(14-CH$_3$); 2.54(N=C(C$\underline{H}_3$)CH$_2$); 2.59(N(C$\underline{H}_2$C$\overline{H}_3$)$_2$); 2.82(C$\underline{H}_2$N(CH$_2$C$\overline{H}_3$)$_2$); 4.93(14-$\underline{H}$); 5.10 and 5.22(5-C$\underline{H}_2$); 7.68(10-$\underline{H}$).

EXAMPLE 2

3-Diethylaminopropan-2-one,[5,8,13,14-tetrahydro-8,13-dioxo-14-methylbenz[5,6]isoindolo[2,1-b]isoquinolin-9-yl]hydrazone (0.07 g). N.m.r. in CDCl$_3$(ppm) δ 1.08 (N(CH$_2$C$\underline{H}_3$)$_2$); 1.56(14-C$\underline{H}_3$); 2.13

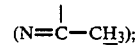
$(\text{N}=\overset{|}{\text{C}}-\text{CH}_3)$;

2.58(N(C$\underline{H}_2$CH$_3$)$_2$); 3.28(N=C(CH$_3$)C$\underline{H}_2$); 4.97(14-$\underline{H}$) 5.14 and $\overline{5}$.25 (5-C$\underline{H}_2$); 7.69(10-$\underline{H}$).

The title compound was prepared by the method of Example 1 from Intermediate 2 (0.3 g) and 3-diethylaminopropan-2-one.

EXAMPLE 3

Acetone,
[5,8,13,14-tetrahydro-8,13-dioxo-14-methylbenz[5,-6]isoindolo[2,1-b]isoquinolin-9-yl]hydrazone (0.85 g).

N.m.r. in COCl$_3$(ppm) δ 1.48(14-C$\underline{H}_3$); 2.09 and 2.13(N=C(C$\underline{H}_3$)$_2$); 4.96(14-$\underline{H}$); 5.12 and 5.22 (5-C$\underline{H}_2$); 7.68(10-$\underline{H}$); 12.33(—N$\underline{H}$).

The title compound was prepared by the method of Example 1 from Intermediate 2 (1.0 g) and acetone except that no p-toluenesulphonic acid was added.

EXAMPLE 4

4-Diethylaminobutan-2-one,[5,8,13,14-tetrahydro-8,13-dioxo-14-methylbenz[5,6]isoindolo[2,1-b]isoquinolin-9-yl]hydrazone, hydrochloride The product of Example 1 (0.7 g dissolved in ethyl acetate (75 ml) was treated portionwise with stirring with a solution of hydrogen chloride in ether until no more precipitation occurred. The resultant orange solid was collected by filtration, washed with ether and dried in vacuo at 20° to give the title compound (0.7 g). N.m.r. in DMSO$_{d6}$ (ppm) δ 1.27 (N(CH$_2$C$\underline{H}_3$)$_2$); 1.49(14-C$\underline{H}_3$);

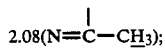

2.08(N=C—C$\underline{H}_3$);

4.82(14-$\underline{H}$); 5.33 and 5.43 (5-C$\underline{H}_2$). U.v. λ$_{max}$ in H$_2$O, 240 nm, $\overline{E}_1^1$646; 274 nm, E$_1^1$ 295; 390 nm, E$_1^1$ 68; 495 nm, E$_1^1$ 141.

EXAMPLE 5

[N-(2-(Diethylamino)ethyl)-N-[5,8,13,14-tetrahydro-8,13-dioxo-14-methylbenz[5,6]isoiodolo[2,1-b]isoquinolin-9-y-]]trifluoroacetamide Intermediate 3 (2.2 g) suspended in acetonitrile (220 ml) was stirred at 20° and treated with freshly prepared N-chloroethyl diethylamine (1.5 g) and powdered potassium hydroxide (0.62 g). After 1½ hours the reaction mixture was poured into water and extracted with ether. The extracts were washed with water, dried and evaporated to dryness. The residue was taken up in ethyl acetate, washed with water containing a little brine, then separated, dried and evaporated. Trituration with a mixture of ether and light petroleum caused the crystallisation of a yellow solid. This was collected to give the title compound (2 g). N.m.r. in CDCl$_3$(ppm) δ 1.58(14-C$\underline{H}_3$); 4.97(14-$\underline{H}$); 5.19 and 5.27(5-C$\underline{H}_2$); 3.14 and

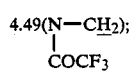

4.49(N—C$\underline{H}_2$);
    |
    COCF$_3$ 2.63 and 2.81 (C$\underline{H}_2$N(CH$_2$CH$_3$)$_2$); 2.50(N(C$\underline{H}_2$CH$_3$)$_2$); 0.97(N(CH$_2$C$\underline{H}_3$)$_2$).

EXAMPLE 6

[N-(2-(N-Ethyl, N-2-benzoylethyl)aminoethyl)-N-[5,8,13,14-tetrahydro-8,13-dioxo-14-methylbenz[5,6]isoindolo[2 1-b]isoquinolin-9-yl]]trifluoroacetamide A mixture of Intermediate 3 (1.2 g) and N-chloroethyl-N-2-benzoyloxyethylethylamine (1.5 g) suspended in acetonitrile (120 ml) was stirred at 20° during addition of powdered potassium hydroxide (0.3 g). Stirring was continued for 1 hr, water was added followed by extraction with ethyl acetate. Separation of the organic phase and evaporation of solvents afforded a dark residue which was purified by chromatography on silica gel. Elution with dichloromethane to remove less polar impurities followed by 2% methanol in dichloromethane afforded the title compound (650 mg) as a dark viscous oil. N.m.r. in CDCl$_3$(ppm) δ 1.5–1.7(14-C$\underline{H}_3$); 1.5–1.7(NCH$_2$C$\underline{H}_3$); 4.97(14-$\underline{H}$); 5.16 and 5.26(5-C$\underline{H}_2$): 4.31(C$\underline{H}_2$OCOPh).

EXAMPLE 7

5,8,13,14-Tetrahydro-9-(2-(diethylamino)ethylamino)-14-methylbenz[5,6]isoindolo[2,1-b]isoquinoline-8,13-dione The product of Example 5 (1.5 g) dissolved in methanol (75 ml) was heated to reflux temperature then stirred during the addition of sodium hydroxide (0.23 g) in water (3 ml). The mixture was heated under reflux for 20 minutes and then the solvents were removed under reduced pressure. The residue was chromatographed on silica gel, eluting with a mixture of ethyl acetate and methanol (10:1) to give the title compound as a bright orange crystalline solid (0.9 g). N.m.r. in CDCl$_3$(ppm) δ 1.54(14-C$\underline{H}_3$); 4.96(14-$\underline{H}$); 5.13 and 5.23(5-C$\underline{H}_2$); 6.98(10-$\underline{H}$); 3.39(NHC$\underline{H}_2$); 2.80(C$\underline{H}_2$N(CH$_2$CH$_3$)$_2$): 2.64(N(C$\underline{H}$CH$_3$)$_2$); 1.10 N(CH$_2$C$\underline{H}_3$)$_2$). U.v. λ$_{max}$ 235 nm, E$_1^1$ 1012; 261 nm, E$_1^1$ 358; 308 nm, E$_1^1$ 159; 375 nm, E$_1^1$ 99; 483 nm, E$_1^1$ 220.

EXAMPLE 8

5,8,13,14-Tetrahydro-9-(2-((N-ethyl,N-2-hydroxyethyl)amino)ethylamino)-14-methylbenz[5,6]isoindolo[2,1-b]isoquinoline-8,13-dione The product of Example 6 (640 mg) in methanol (32 ml) was heated to reflux then treated with aqueous sodium hydroxide (0.12 g in 1.5 ml water). Heating was continued for 20 mins. and then the solvents were removed in vacuo. The residue was chromatographed on silica gel eluting with ethyl acetate/methanol (10:1) to afford a red gum which crystallised on trituration with ether to give the title compound (150 mg) as an orange solid. N.m.r. in CDCl$_3$(ppm) δ 1.54(14-C$\underline{H}_3$): 4.94(14-$\underline{H}$); 5.09,5.21(5-C$\underline{H}_2$); 6.92(10-$\underline{H}$); 3.37(NHC$\underline{H}_2$); 2.87(NCH$_2$C$\underline{H}_2$OH); 3.66(CH$_2$C$\underline{H}_2$OH). U.v. λ$_{max}$ 235 nm, E$_1^1$997; 261 nm, E$_1^1$ 349: 309 nm, E$_1^1$ 154, 375 nm, E$_1^1$ 98; 484 nm, E$_1^1$ 214.

EXAMPLE 9

5,8,13,14-Tetrahydro-9-(2-(diethylamino)ethylamino)-14-methylbenz[5,6]isoindolo[2,1-b]isoquinoline-8,13-dione, hydrochloride The product of Example 7 (0.9 g dissolved in ethyl acetate (200 ml) was treated portionwise with stirring with a solution of hydrogen chloride in ether until precipitation ceased. The solid was collected by filtration, washed with anhydrous ether and dried in vacuo at 20° to give the title compound as an orange solid (0.95 g). N.m.r. in (CF$_3$CO)$_2$O (ppm) δ 1.63(14-C$\underline{H}_3$): 1.58(N(CH$_2$C$\underline{H}_3$)$_2$); 3.58(N(C$\underline{H}_2$CH$_3$)$_2$); 4.09(C$\underline{H}_2$N(CH$_2$CH$_3$)$_2$); 4.26(NHC$\underline{H}_2$); 5.09(14-$\underline{H}$); 5.34(5-C$\underline{H}_2$). U.v. λ$_{max}$ in H$_2$O 236 nm, E$_1^1$ 725; 273 nm, E$_1^1$ 307; 307 nm, E$_1^1$ 97; 381 nm, E$_1^1$87; 475 nm, E$_1^1$ 190.

EXAMPLE 10

5,8,13,14-Tetrahydro-9-(2-((N-ethyl N-2-hydroxyethyl)amino)ethylamino)-14-methyl-benz[5,6]isoindolo[2,1-b]isoquinoline-8,13-dione, hydrochloride The product of Example 8 (130 mg) in warm ethyl acetate (25 ml) was cooled to 20° before dilution with ether and treatment with a slight excess of anhydrous hydrogen chloride in ether. The precipitated orange solid was collected by filtration, washed with ether and dried in vacuo to give the title compound (132 mg). N.m.r. in CDCl$_3$(ppm) δ 1.35–1.60(14-CH$_3$); 1.35–1.60(N(CH$_2$CH$_3$)$_2$); 3.99(NHCH$_2$); 4.09(CH$_2$OH); 4.83(14-H); 5.08 and 5.16(5-CH$_2$). U.v. λ$_{max}$ in H$_2$O 236 nm, E$_1^1$ 634; 273 nm, E$_1^1$ 266; 475 nm, E$_1^1$ 168.

EXAMPLE 11

[(N-(2-(N-Ethyl, N-2-hydroxyethyl)aminoethyl)-N-[5,8,13,14-tetrahydro-8,13-dioxo-14-methylbenz[5,6]isoindolo[2,1-b]isoquinolio-9-yl]]trifluoroacetamide, hydrochloride The product of Example 6 (0.5 g) in dioxan (50 ml) was treated dropwise with 10N-hydrochloric acid until a slight excess of acid was present. Excess ether was then added to the mixture whereupon a solid precipitated. Collection of the solid by filtration and washing with ether afforded the title compound (200 mg) as a pale green solid. N.m.r. in (CF$_3$CO)$_2$O (ppm) δ 1.63(14-CH$_3$); 1.53(NCH$_2$CH$_3$); 5.02(14-H); 5.28 and 5.38(5-CH$_2$); 7.79(10-H).

EXAMPLE 12

N-[5,8,13,14-Tetrahydro-8,13-dioxobenz[5,6isoindolo[2.1-b]isoquinolin-9(or12)-yl]-1-diethylamino acetamide Intermediate 10 (1.0 g) was suspended in acetone (200 ml) then treated at 20° with diethylamine (0.43 ml) stoppered and stirred at 20° for 18 hours. The resulting suspension was filtered, the filtrate was evaporated and the residue was treated with a little acetone to give a solid which was collected by filtration and washed lightly with acetone to give the title compound as a yellow/green solid (200 mg), m.p.>300°. U.v. λ$_{max}$ 253 nm, E$_1^1$942 and 395 nm, E$_1^1$282.

Examples 13, 14 17 and 18 were prepared in a similar manner.

EXAMPLE 13

4-Methyl-N-[5,8,13,14-tetrahydro-8,13-dioxobenz[5,6]-isoindolo[2,1-b]isoquinolin-9(or 12)-yl]piperazine-1-acetamide (0.42 g), m.p.>300°. U.v. λ$_{max}$ 253 nm, E$_1^1$609 and 396.5 nm, E$_1^1$184.

From Intermediate 10 (0.5 g) and N-methylpiperazine (0.2g).

EXAMPLE 14

N-[5,8,13,14-Tetrahydro-8,13-dioxobenz[5,6]isoindolo[2,1-b]isoquinolin-9(or 12)-yl]morpholine acetamide (150 mg), m.p. >300°. U.v. λ$_{max}$ 253 nm, E$_1^1$ 490 and 395 nm, E$_1^1$ 190.

From Intermediate 10 (500 mg) and morpholine (0.18 g).

EXAMPLE 15

4-Methyl-N-[5,8,13,14-tetrahydro-8,13-dioxobenz[5,-6]isoindolo[2,1-b]isoquinolin-9(or 12)-yl]piperazine-1-acetamide, dihydrochloride The compound of Example 13 (350 mg) was stirred and warmed in water (250 ml) containing concentrated hydrochloric acid (about 1.5 ml). then filtered and the filtrate evaporated. The resulting green residue was triturated with ether containing sufficient ethanol to keep the particles separate and filtered to give a solid which was washed (2x) with anhydrous ether and sucked dry to give the title compound (180 mg) m.p.>300°. U.v. λ$_{max}$ (water) 255 nm, E$_1^1$ 452 and 403 nm, E$_1^1$ 126.

EXAMPLE 16

N-[5,8,13,14-tetrahydro-8,13-dioxobenz[5,6]isoindolo[2,1-b]isoquinolin-9(or12)-yl]-1-diethylamino acetamide, hydrochloride The compound of Example 12 (0.7 g) was dissolved with warming in dioxan (70 ml), filtered, then cooled and treated with concentrated hydrochloric acid 10.18 ml). The mixture was diluted with anhydrous ether (70 ml) allowed to stand for 1 hour and then filtered to give a solid which was washed with anhydrous ether and sucked dry to yield the title compound (0.7 g), m.p.>300°. U.v. λ$_{max}$ (water) 257.5 nm, E$_1^1$ 378 and 414.5 nm E$_1^1$ 155.

Examples 22–26 were prepared in a similar manner.

EXAMPLE 17

N-[5,8,13,14-Tetrahydro-8,13-dioxo-14-methylbenz[5,-6]isoindolo[2,1-b]isoquinoline-9-yl]-1-diethylamino acetamide (185 mg). U.v. λ$_{max}$ 254 nm, E$_1^1$ 831; 394 nm, E$_1^1$ 268.

From Intermediate 5 (360 mg) and diethylamine (0.2 ml).

EXAMPLE 18

N-[5,8,13,14-Tetrahydro-8,13-dioxo-14-methylbenz[5,-6]isoindolo[2,1-b]isoquinolin-12-yl]-1-diethylamino acetamide (3.05 g). U.v. λ$_{max}$ 252.5 nm, E$_1^1$ 1 855; 394 nm, E$_1^1$ 248.

From the 12-Isomer of Intermediate 11 (3.6 g) and diethylamine (1.5 ml in 15 ml acetone).

EXAMPLE 19

N-[5.8,13,14-Tetrahydro-8,13-dioxo-14-methylbenz[5,-6]isoindolo[2,1-b]-isoquinolin-12-yl]-1-dimethylaminoethylamino acetamide The 12-isomer of Intermediate 11 in dichloromethane (80 ml) was treated with N,N-dimethylethylene diamine (1.76 g) and the mixture was heated under reflux for 1.5 hours. After cooling the mixture was diluted to 1.5 liters with dichloromethane and then washed with aqueous sodium bicarbonate. The organic solution was dried and evaporated and the resultant product was purified by chromatography on silica gel (dichloromethane/methanol/aqueous ammonia solution, 91.5:7.5:1) to give the title compound as an orange/yellow solid (383 mg). U.v. λ$_{max}$ 253.5 nm, E$_1^1$ 813; 397.5 nm, E$_1^1$ 246.

Examples 20 and 21 were prepared in a similar manner.

EXAMPLE 20

N-[5,8,13,14-Tetrahydro-8,13-dioxohenz[5,6]isoindolo[2,1-b]isoquinolin-12-yl]-1-dimethylaminoethylamino acetamide (0.58 g). U.v. $\lambda_{max}$ 252.5 nm, $E_1^1$ 828; 394 nm, $E_1^1$ 250.

From Intermediate 10 (1.93g).

EXAMPLE 21

N-[5,8,13,14-Tetrahydro-8,13-dioxobenz[5,6]isoindolo[2,1-b]isoquinolin-12-yl]-1-(2-hydroxyethylamino acetamide (0.19 g). U.v. $\lambda_{max}$ 253 nm, $E_1^1$ 820; 396 nm, $E_1^1$303.

From Intermediate 10 (0.30 g) and ethanolamine.

EXAMPLE 22

N-[5,8,13,14-Tetrahydro-8,13-dioxo-14-methylbenz[5,6]isoindolo[2,1-b]isoquinolin-9-yl]-1-diethylamino acetamide, hydrochloride (181 mg). U.v. $\lambda_{max}$ 254.5 nm, $E_1^1$ 623: 400 nm, $E_1^1$ 178.

From the compound of Example 17 (177 mg) and 10N hydrochloric acid (3 drops).

EXAMPLE 23

N-[5,8,13,14-Tetrahydro-8,13-dioxo-14-methylbenz[5,6]isoindolo[2,1-b]isoquinolin-12-yl]-1-diethylamino acetamide hydrochloride (3 g).

U.v, $\lambda_{max}$ 254.5 nm, $E_1^1$ 679: 402 nm, $E_1^1$223.
From the compound of Example 18 (3 g).

EXAMPLE 24

N-[5,8,13,14-Tetrahydro-8,13-dioxo-14-methylbenz[5,6]isoindolo[2,1-b]isoquinolin-12-yl]-1-dimethylaminoethylamino acetamide, dihydrochloride (0.45 g). U.v. $\lambda_{max}$ 252 nm, $E_1^1$ 586; 396 nm, $E_1^1$ 171.

From the compound of Example 19 (0.39 g).

EXAMPLE 25

N-[5,8,13,14-Tetrahydro-8,13-dioxobenz[5,6]isoindolo[2,1-b]isoquinolin-12-yl]-1-dimethylaminoethylamino acetamide, hydrochloride (0.56 g). U.v. $\lambda_{max}$ 255.5 nm, $E_1^1$632; 407 nm, $E_1^1$ 180.

From the compound of Example 20 (0.52g) and 1 molar equivalent of concentrated hydrochloric acid.

EXAMPLE 26

N-[5,8,13,14-Tetrahydro-8,13-dioxobenz[5,6]isoindolo[2,1-b]isoquinolin-12-yl]-1-(2-hydroxyethylamino)acetamide hydrochloride (0.32 g). U.v. max 252.5 nm, $E_1^1$ 630; 397 nm, $E_1^1$ 193.

From the compound of Example 21 (0.37 g).

The following are examples of pharmaceutical compositions according to the invention. The term 'Active ingredient' as used hereinafter means a compound of the invention and may be for example the compound of Examples 1 or 8 or the corresponding hydrochloride salts of Examples 4 and 10 respectively.

| Example A-Dry Powder for Injection | |
|---|---|
| | mg/vial |
| Active ingredient | equivalent to 100 mg base |
| Sodium phosphate, anhydrous | 3.5 |
| Citric acid, anhydrous | 3.7 |

Method 1

Blend the sterile ingredients until homogeneous. Fill aseptically into glass vials. Purge the headspace with nitrogen and close the vials using rubber closures and metal overseals.

Method 2

Dissolve the ingredients in water for injections B.P. Sterilise the solution by membrane filtration. Aseptically fill into freeze-drying vials and place suitable rubber freeze-drying closures in position. Freeze-dry, filling the vials with nitrogen at the end of the cycle. Fully insert the closures and apply metal overseals.

Constitution

Constitute with a suitable sterile vehicle, e.g. using water for injections or using a 53 w/v dextrose solution, as an injection (e.g. in a 10 ml volume) or an infusion (e.g. in a 100 ml volume).

| Example B - Oral Tablet | |
|---|---|
| | mg/tablet |
| Active Ingredient | equivalent to 250 mg base |
| Sodium starch glycolate | 6 |
| Magnesium stearate | 2 |
| Microcrystalline cellulose | to 500 mg |

Sieve the ingredients and blend until homogeneous. Compress with appropriate punches. The tablets may be covered with a thin polymer coat applied by the usual film coating techniques. A pigment may be included in the film coat.

I claim:

1. A compound of formula (1)

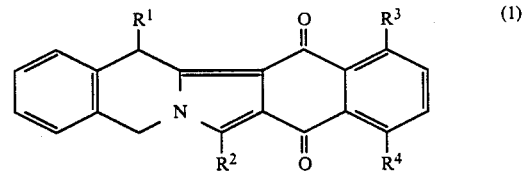

wherein
$R^1$ is a hydrogen atom or a methyl group;
$R^2$ is a hydrogen or halogen atom or a methyl group; and one of $R^3$ and $R^4$ is a hydrogen atom and the other is a group —$NR^5R^6$ (where $R^5$ is a hydrogen atom and $R^6$ is a group —$COCH_2NR^7R^8$ (wherein $R^7$ and $R^8$, which may be the same or different, each represents a hydrogen atom or a $C_{3-7}$ cycloalkyl group or a $C_{1-4}$ alkyl group optionally substituted by a hydroxyl or benzoyloxy group), or $R^6$ is a group —$COCH_2NH(CH_2)_nNR^7R^8$ (where n is an integer from 2 to 5 inclusive and $R^7$ and $R^8$ are as defined above), or $R^6$ is a group —$N=CR^9R^{10}$ (where $R^9$ is a hydrogen atom or a $C_{1-4}$ alkyl group and $R^{10}$ is a $C_{1-4}$ alkyl group optionally substituted by a group —$NR^7R^8$ and $R^7$ and $R^8$ are as defined above) or $R^5$ is a hydrogen atom, a benzoyl group, a phenyl $C_{1-6}$ alkanoyl group, a $C_{1-6}$ alkanoyl group, or a halogenated $C_{1-6}$ alkanoyl group, and $R^6$ is a group —$(CH_2)_nNR^7R^8$ (where n, $R^7$ and $R^8$ are as defined above)) or a salt thereof.

2. A compound of formula (1) as claimed in claim 1 wherein $R^5$ is a hydrogen atom, a benzoyl group, a phenyl $C_{1-6}$ alkanoyl group, a $C_{1-6}$ alkanoyl group, or a halogenated $C_{1-6}$ alkanoyl group, and $R^6$ is a group —$(CH_2)_nNR^7R^8$, wherein n, $R^7$ and $R^8$ are defined in claim 1, or a salt thereof.

3. A compound of formula (1) as claimed in claim 1 wherein $R^5$ is a hydrogen atom and $R^6$ is a group —$COCH_2NR^7R^8$ or —$COCH_2NH(CH_2)_nNR^7R^8$ (where n is an integer from 2 to 5 inclusive and $R^7$ and $R^8$, which may be the same or different, each represents a hydrogen atom or a $C_{3-7}$ cycloalkyl group or a $C_{1-4}$ alkyl group optionally substituted by a hydroxyl group), or a salt thereof.

4. A compound of formula (1) as claimed in claim 2 wherein $R^5$ is a hydrogen atom and $R^7$ and $R^8$, which may be the same or different, each represents a methyl, ethyl or hydroxyethyl group, or a salt thereof.

5. A compound of formula (1) as claimed in claim 3 wherein $R^5$ is a hydrogen atom and $R^7$ and $R^8$, which may be the same or different, each represents a methyl, ethyl or hydroxyethyl group, or a salt thereof.

6. A compound of formula (1) as claimed in claim 1 wherein $R^5$ is hydrogen and $R^6$ is a group —$N=CR^9R^{10}$ (where $R^9$ is a hydrogen atom or a $C_{1-4}$ alkyl group and $R^{10}$ is a $C_{1-4}$ alkyl group optionally substituted by a group —$NR^7R^8$ where $R^7$ and $R^8$, which may be the same or different, each represents a hydrogen atom or a $C_{3-7}$ cycloalkyl group or a $C_{1-4}$ alkyl group optionally substituted by a hydroxyl group), or a salt thereof.

7. A compound of formula (1) as claimed in claim 6 wherein $R^9$ is a hydrogen atom and $R^7$ and $R^8$, which may be the same or different, each represents a methyl, diethylaminomethyl or diethylaminoethyl group, or a salt thereof.

8. A compound of formula (1) as claimed in claim 1 wherein $R^1$ is a methyl group, or a salt thereof.

9. A compound of formula (1) as claimed in claim 1 wherein $R^2$ is a hydrogen atom, or a salt thereof.

10. A compound of formula (1) as claimed in claim 1 wherein $R^3$ is a hydrogen atom, or a salt thereof.

11. A compound as claimed in claim 1 being 5,8,13,14-tetrahydro-9-(2-((N-ethyl,N-2-hydroxyethyl)-amino)ethylamino)-14-methylbenz[5,6]isoindolo[2,1-b]iso-quinoline-8,13-dione, or a physiologically acceptable salt thereof.

12. A compound as claimed in claim 11 being a hydrochloride salt of 5,8,13,14-tetrahydro-9-(2-((N-ethyl,N-2-hydroxyethyl)-amino)ethylamino)-14-methylbenz[5,6]isoindolo[2,1-b]isoquinoline-8,13-dione.

13. A compound as claimed in claim 1 being 4-diethylaminobutan-2-one,5,8,13,14-tetrahydro-8,13-dioxo-14-methylbenz[5,6]isoindolo[2,1-b]iso-quinoline-9-yl]hydrazone, or a physiologically acceptable salt thereof.

14. A compound as claimed in claim 13 being a hydrochloride salt of 4-diethylaminobutan-2-one,5,8,13,14-tetrahydro-8,13-dioxo-14-methylbenz[5,6]isoindolo[2,1-b]iso-quinoline-9-yl]hydrazone.

15. A pharmaceutical composition comprising as an active ingredient a compound of formula (1) (as defined in claim 1) or a physiologically acceptable salt thereof, together with one or more pharmaceutical carriers or excipients.

16. A composition as claimed in claim 15 adapted for parental administration.

17. A compound of formula (9)

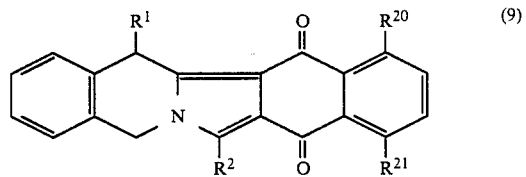

(wherein one of $R^{20}$ and $R^{21}$ is a hydrogen atom and the other is a group —$NHR^5$, —$NHNH_2$, —$NHCOCH_2L$ (where L is a leaving group) or —$NO_2$ and $R^1$, $R^2$ and $R^5$ are as defined in claim 1).

* * * * *